United States Patent
Bonfils-Rasmussen

(10) Patent No.: US 12,350,069 B2
(45) Date of Patent: *Jul. 8, 2025

(54) SYSTEM AND METHOD FOR LAPAROSCOPIC NERVE IDENTIFICATION, NERVE LOCATION MARKING, AND NERVE LOCATION RECOGNITION

(71) Applicant: ProPep Surgical, LLC, Austin, TX (US)

(72) Inventor: Jann Bonfils-Rasmussen, Leander, TX (US)

(73) Assignee: ProPep Surgical, LLC, Austin, TX (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/234,163

(22) Filed: Apr. 19, 2021

(65) Prior Publication Data

US 2021/0236055 A1 Aug. 5, 2021

Related U.S. Application Data

(63) Continuation of application No. 15/323,356, filed as application No. PCT/US2015/041213 on Jul. 20, 2015, now Pat. No. 10,987,050.

(Continued)

(51) Int. Cl.
*A61B 1/00* (2006.01)
*A61B 1/313* (2006.01)
(Continued)

(52) U.S. Cl.
CPC ...... *A61B 5/4893* (2013.01); *A61B 1/000094* (2022.02); *A61B 1/00045* (2013.01); *A61B 1/3132* (2013.01); *A61B 5/6877* (2013.01); *A61B 18/1206* (2013.01); *A61B 34/30* (2016.02); *A61B 90/361* (2016.02); *A61B 90/37* (2016.02); *A61B 90/39* (2016.02); *A61B 2018/00595* (2013.01);

(Continued)

(58) Field of Classification Search
CPC .......... A61B 1/000094; A61B 1/00045; A61B 1/3132; A61B 5/4893; A61B 8/1206; A61B 2018/00595; A61B 2034/2065; A61B 5/743; G06T 7/0014
See application file for complete search history.

(56) References Cited

U.S. PATENT DOCUMENTS

| 4,962,766 | A | 10/1990 | Herzon |
| 5,178,145 | A | 1/1993 | Rea |

(Continued)

FOREIGN PATENT DOCUMENTS

KR  10-2014-0077029 A   6/2014

OTHER PUBLICATIONS

Science Daily, "Nerve Mapping Technology Improves Surgery for Compressed Nerves," Science Daily, Mar. 23, 2013, 2 pages, https://www.sciencedaily.com/releases/2013/03/130323152444.htm.

(Continued)

*Primary Examiner* — Anh Tuan T Nguyen
*Assistant Examiner* — Rynae E Boler
(74) *Attorney, Agent, or Firm* — Trop, Pruner & Hu, P.C.

(57) ABSTRACT

A method and system for nerve identification, monitoring, location marking, and location recognition system used during laparoscopic surgery.

20 Claims, 2 Drawing Sheets

Related U.S. Application Data

(60) Provisional application No. 62/027,130, filed on Jul. 21, 2014.

(51) Int. Cl.

| | | |
|---|---|---|
| *A61B 5/00* | (2006.01) | |
| *A61B 18/12* | (2006.01) | |
| *A61B 34/30* | (2016.01) | |
| *A61B 90/00* | (2016.01) | |
| *A61B 18/00* | (2006.01) | |
| *A61B 18/14* | (2006.01) | |
| *A61B 34/20* | (2016.01) | |

(52) U.S. Cl.
CPC ............ *A61B 2018/00642* (2013.01); *A61B 2018/00839* (2013.01); *A61B 18/1482* (2013.01); *A61B 2034/2065* (2016.02); *A61B 2034/302* (2016.02); *A61B 2090/3612* (2016.02); *A61B 2090/363* (2016.02); *A61B 2090/364* (2016.02); *A61B 2090/368* (2016.02); *A61B 2090/3937* (2016.02)

(56) References Cited

U.S. PATENT DOCUMENTS

| | | | |
|---|---|---|---|
| 6,425,865 B1 | 7/2002 | Salcudean et al. | |
| 6,466,817 B1 | 10/2002 | Kaula et al. | |
| 6,493,588 B1 | 12/2002 | Malaney et al. | |
| 6,609,018 B2 | 8/2003 | Cory et al. | |
| 7,104,965 B1 | 9/2006 | Jiang et al. | |
| 7,789,833 B2 | 9/2010 | Urbano et al. | |
| 8,083,685 B2 | 12/2011 | Fagin | |
| 9,022,948 B2 | 5/2015 | Wang | |
| 9,042,978 B2 | 5/2015 | Wu et al. | |
| 9,327,123 B2 | 5/2016 | Yamasaki et al. | |
| 9,622,684 B2 | 4/2017 | Wybo | |
| 9,743,884 B2 | 8/2017 | Rasmussen | |
| 10,016,142 B2 | 7/2018 | Block et al. | |
| 10,045,704 B2 | 8/2018 | Fagin et al. | |
| 2008/0065107 A1 | 3/2008 | Larkin | |
| 2008/0082109 A1* | 4/2008 | Moll | A61B 34/37 606/130 |
| 2008/0183190 A1 | 7/2008 | Adcox et al. | |
| 2009/0105708 A1 | 4/2009 | Mcginnis et al. | |
| 2010/0010367 A1 | 1/2010 | Foley et al. | |
| 2011/0060243 A1 | 3/2011 | Hausman et al. | |
| 2011/0270120 A1* | 11/2011 | McFarlin | A61B 5/4893 600/554 |
| 2011/0276058 A1 | 11/2011 | Choi et al. | |
| 2012/0109004 A1* | 5/2012 | Cadwell | A61B 8/5261 600/554 |
| 2012/0283732 A1 | 11/2012 | Lam | |
| 2014/0316268 A1 | 10/2014 | Kafiluddi et al. | |
| 2018/0028804 A1 | 2/2018 | Pianca | |
| 2018/0242910 A1 | 8/2018 | Marcotte et al. | |
| 2018/0289277 A1 | 10/2018 | Whittaker et al. | |
| 2018/0344244 A1 | 12/2018 | Botzer et al. | |

OTHER PUBLICATIONS

The Neurosurgery Spine Center, "Nerve Mapping," Dec. 5, 2017, 3 pages, https://www.neurosurgeryspinecenter.com/nerve-mapping/.

Raymond P. Onders, et al., "Mapping the phrenic nerve motor point: The key to a successful laparoscopic diaphragm pacing system in the first human series," Department of Surgery, University Hospitals of Cleveland, Cleveland, Ohio, Oct. 2004, 8 pages.

International Search Report and Written Opinion dated Oct. 22, 2015, issued in corresponding International Application No. PCT/US2015/041213 (12 pages).

* cited by examiner

SYSTEM AND METHOD FOR LAPAROSCOPIC NERVE IDENTIFICATION, NERVE LOCATION MARKING, AND NERVE LOCATION RECOGNITION

This application is a continuation of U.S. patent application Ser. No. 15/323,356, filed Dec. 30, 2016 and entitled "System and Method for Laparoscopic Nerve Identification, Nerve Location Marking, and Nerve Location Recognition," which is a § 371 National Stage Entry of International Application No. PCT/US2015/041213, filed Jul. 20, 2015, which claims priority to U.S. Provisional Application No. 62/027,130, filed Jul. 21, 2014 and entitled "Dual Function Electrosurgical Nerve Identification, Nerve Monitoring and Optical Assisted Nerve Location Marking and Nerve Location Recognition System." The content of each of the above applications is hereby incorporated by reference.

BACKGROUND

Traditionally, surgery on internal body parts is performed by cutting an incision in the skin to access the internal body parts. Such open surgery entails a number of known risks including infection, inadvertent damage to other organs, nerves and other structures, scarring, and loss of blood. In an effort to reduce some of these risks and improve patient outcomes surgeons have developed laparoscopic, and more recently robotic techniques to perform surgery. Robotic surgery is essentially an advanced type of laparoscopic surgery in which the arms that enter the body cavity are robotically controlled instead of manually controlled. During a laparoscopic or robotic surgery, such as the da Vinci® surgery system, small incisions are made in the skin through which 5-12 millimeter access ports are placed. These ports serve as doorways through which small working instruments and an optical element can be placed. The optical element/camera creates a magnified view of the internal organs that the surgeon sees on a monitor or console. Such less invasive laparoscopic and robotic surgeries typically have reduced side effects for the patient to allow a more rapid and complete recovery. They have not, however, substantially decreased the incidence of intraoperative nerve damage that has been attributed to post-surgery side effects such as paralysis, erectile dysfunction, and urinary and fecal incontinence.

This inadvertent nerve damage often occurs because the surgeon cannot identify the nerves during surgery because they are either buried in tissue and/or are too small to be seen with the naked eye or with the magnification typically used during laparoscopic and robotic surgery. This problem is complicate in laparoscopic and robotic surgery because not only can the surgeons not see the nerves but, because their hands are not in the surgical field, they cannot palpate them either.

This problem of inadvertent nerve damage during surgery gave birth to the intraoperative neuromonitoring industry over 20+ years ago. Since that time, intraoperative nerve identification and monitoring has become standard of care in open surgical procedures in spine, ENT, vascular and many other surgical specialties. Until recently, however, intraoperative nerve monitoring was not performed during laparoscopic or robotic surgery. This changed with the introduction of the ProPep Nerve Monitoring System. This System allows nerve identification and nerve monitoring to be performed in real-time during both robotic-assisted and traditional laparoscopic surgery. Unfortunately, the system does not "remember" or mark where the nerves are when the surgeon moves the laparoscopic/robotic optical element, changing his view of the anatomy. This is cumbersome for the surgeon and can increase the procedure time as the surgeon has to reaffirm the location of the nerve throughout a surgical procedure.

SUMMARY

This application addresses this shortcoming by coupling optical digital image marking and position and image recognition software with an intraoperative neuromonitoring system such as the ProPep Surgical nerve monitoring system.

In a robotic-assisted surgery, the surgeon is "viewing" the tissue of interest using an optical element connected to a camera. The system works by allowing the surgeon to digitally "mark" the location of a nerve in a visual field associated with a specific location, magnification and orientation of the robotic-assisted optical element when the surgeon identifies a nerve using an intraoperative neuromonitoring system. If the surgeon moves the optical element after "marking" the nerve location in order to facility some aspect of the surgery, he/she can return the optical element to the position it was in when the location of the nerve was "marked" by activating a Recall Switch. This not only returns the optical element to the original position (via the position recognition software) but also returns it to the original magnification and re-displays the nerve location in the surgeon's visual field.

In a manually operated laparoscopic surgery the system will work in a similar manner. The surgeon is now manually controlling the movement of the optical element and will digitally "mark" the location of a nerve in a visual field after identifying the nerve with an intraoperative neuromonitoring system. If the surgeon moves the optical element after "marking" the nerve location in order to facility some aspect of the surgery, he/she can physically reposition the optical element to the position it was in when the location of the nerve was "marked" via the image recognition software. The surgeon can then use a Re-Display Switch to re-display the nerve location in the surgeon's visual field.

The shortcoming can also be met by a method for nerve identification, location marking, and location recognition during laparoscopic surgery including at least: providing an optical element connected to a camera; providing a surgical instrument for use as an exploratory probe; providing at least one electrode probe inserted into a body cavity through a surface of the body, the at least one electrode probe being positionable by a surgical instrument and being operable to couple to muscle tissue within the body cavity; introducing an electrical signal via the surgical instrument operating as an exploratory probe to the muscle tissue within the body cavity along a presumed pathway of a nerve, thereby selectively creating an electrical potential received by the at least one electrode probe coupled to the muscle tissue within the body cavity; displaying the electrical potential; analyzing and evaluating the electrical potential with the analyzer to determine the location of the nerve; capturing an image of the pathway of the nerve; generating and displaying a visual marker of that pathway and storing that image for future reference; saving the exact positioning of the optical element when the visual marker was generated, allowing a return to that exact position through position or image recognition; and re-displaying the visual marker of the nerve pathway upon return of the optical element to the stored position.

The shortcoming can also be addressed by a nerve identification, monitoring, location marking, and location recognition system used during laparoscopic surgery including at least: an optical element connected to a camera and surgeon monitor; at least one recording electrode probe; a surgical instrument for use as an exploratory probe; an analyzer in operable communication with the at least one recording electrode; the analyzer operable to indicate the proximity of the exploratory probe to the nerve based on the strength of an electrical signal sensed by the at least one recording electrode probe; an analyzer monitor to display the electrical signal sensed; an image capture and digital marker system activated by a criteria gate that sets and stores a digitally generated marker at the location of an identified nerve; an image control processor that sends the stored image to be displayed on a surgeon monitor; and an position or image recognition processor operating position or image recognition software that can store the position of the optical element or the image of the surgeon's visual field in the surgeon monitor when the visual marker of the nerves is first generated and redisplay the digitally generated marker of an identified nerve at its location on a surgeon monitor when desired; and a recall or re-display switch that can return the optical element to the position it was in when the visual marker was generated or recognize the image in the surgeon visual field when the optical element is returned to the position it was in when the visual marker was generated, and signal the position or image recognition processor to redisplay the digitally generated marker on the surgeon monitor.

The surgical benefits of using this include the ability for the surgeon to instantly relocate non-visible nerve tissue marked earlier during the surgical procedure so as to know what tissue to spare/not compromise during subsequent surgical intervention and manipulation.

DETAILED DESCRIPTION

Figure 1:
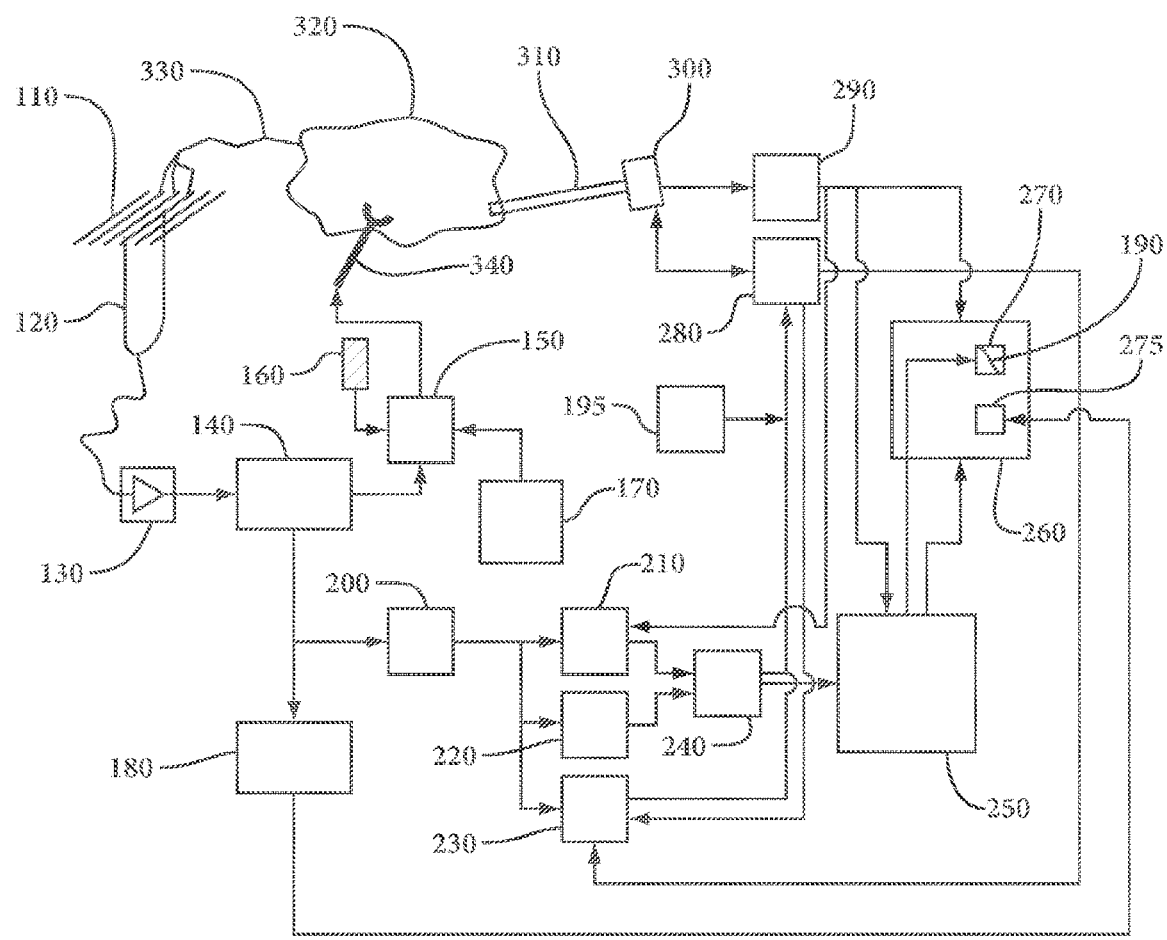
FIG. 1 is an overall schematic illustration of the proposed system and the resultant integration into a robotic-assisted laparoscopic surgery system.

This need, to identify and recall the position of non-visible nerve tissue during laparoscopic surgery, can be met with the system to be described below in reference to FIG. 1. In general many of the elements shown on the left hand side of the drawing are part of the (modified) ProPep Surgical nerve monitoring system. The description of the ProPep system is presented in U.S. Pat. No. 8,083,685, issued on Dec. 7, 2011 and incorporated herein by reference in its entirety.

In accordance with the present disclosure, a system and method are provided which substantially reduces the disadvantages and problems associated with previous methods and systems for identifying non-visible nerve tissue during robotic-assisted laparoscopic surgery.

Referring first to FIG. 1 for a robotic surgery system, numeral 320 represents human tissue located within a body cavity containing non-visible nerve tissue. A dual function laparoscopic surgical instrument 340 from a robotic surgical system is being used to perform laparoscopic surgery within the body cavity and to stimulate tissue. In this context the term dual function refers to the use of the surgical instrument as either an exploratory probe used to stimulate tissue or an electro cautery instrument for surgery. The dual function laparoscopic surgical instrument is connected to a control switch 150, which in turn is connected to both an electro cautery generator 170 (power supply) and an electromyographic analyzer 140. The control switch 150 allows the surgeon to switch the power going to the surgical instrument 340 between the cauterizing energy from the electro cautery generator 170 needed to perform surgery and the stimulation energy from the electromyographic analyzer 140 needed to stimulate tissue for the purpose of identifying and monitoring nerves. The control switch can be triggered by a foot pedal 160 or any appropriate switch. The surgeon is aided in these surgical procedures by an optical element 310 protruding into the body cavity and attached to a camera 300. The optical element facilitates visualization of the laparoscopic surgical field. This element can take many forms but is in general a remotely operated endoscopic imaging system with variable magnification and infinite positioning in 3 dimensional space. It is controlled by the Optical Element Positioning Device 280 in such a way as to be able to return to any previous viewing position through the control of the surgeon. The image information from the optical element/camera is fed via a Video Data Analyzer 290 to the surgeon's view finder 260.

There are numerous other elements of the robotic surgery device that are not shown to simplify the description of the instant application. A representative description of such a device is shown in U.S. application No. 20080065107 A1 (Larkin et. al) published Mar. 13, 2008.

To identify non-visible nerve tissue, two recording electrode probes 120, one active and one reference and both connected to the analyzer 140, are inserted through the body surface via a introducer trocar device and into a body cavity so as to be accessible by a laparoscopic surgical instrument (not necessarily the dual function laparoscopic surgical instrument 340) for placement into muscle tissue 110 wherein the non-visible nerve of interest 330 terminates. The dual function laparoscopic surgical instrument 340 switched to stimulation mode is then used to stimulate the tissue 320 along the presumed nerve pathway. If a nerve 330 is present in the tissue, the electric current causes a depolarization of the nerve, which results in a nerve action potential. The nerve action potential then propagates along the nerve to the neuromuscular junction (the synapse between the nerve and the muscle cell) where a neurotransmitter (acetylcholine) is released in response to the action potential. This neurotransmitter depolarizes the postsynaptic muscle cells creating an electrical potential received by the electrode probes 120, analyzed by the analyzer 140 and displayed as a wave form on the analyzer's display 180, an image of which is sent to electromyography (EMG) Window 275 in the Surgeon's View Finder 260. The relative strength of the electrical potential received at an electrode probe 120 will increase as surgical instrument 340 is placed closer to the nerve 330. Thus by moving the surgical instrument 340 along the presumed nerve pathway, the surgeon maps the actual nerve pathway based upon the strength of the signal received at electrode probes 120 for each position of the surgical instrument 340.

As the nerve pathway becomes evident a criteria gate 200 sends information to an image frame capture system 210, and a digital image marker generator 220 that provides a visual marker of the discovered nerve in the surgeon's visual field. In addition the exact positioning of the optical element 310 at the time of the digitally generated marker setting is stored by an Optical Element Position Data Storage 230. An image control processor 240 sends the image of the surgeon's visual field with the visual markers of the nerves 190 to be displayed to a Surgical Field Window 270 in the surgeon's viewfinder 260. Image and Position Recognition Processor 250 manages all of this and stores the image of the surgeon's visual field and the position of the visual markers of the nerves.

As surgery proceeds, the surgeon operating the robotic surgical element may move the optical element of the camera numerous times but can, at any time, return to the position the optical element was in when the nerve of interest was mapped by activating a Recall Switch 195 that signals the Optical Element Positioning Device 280 to pull the position information from the Optical Element Position Data Storage 230 and position the optical element accordingly. In one embodiment, clicking on the Surgical Field Window 270 in the Surgeon's View Finder 260 activates the Recall Switch 195. Once the Optical Element 310 returns to the position it was in when the nerve of interest was marked, the Image and Position Recognition Processor 250 will redisplay the visual marker of the discovered nerve in the Surgeon View Finder 260 at its location.

Figure 2:
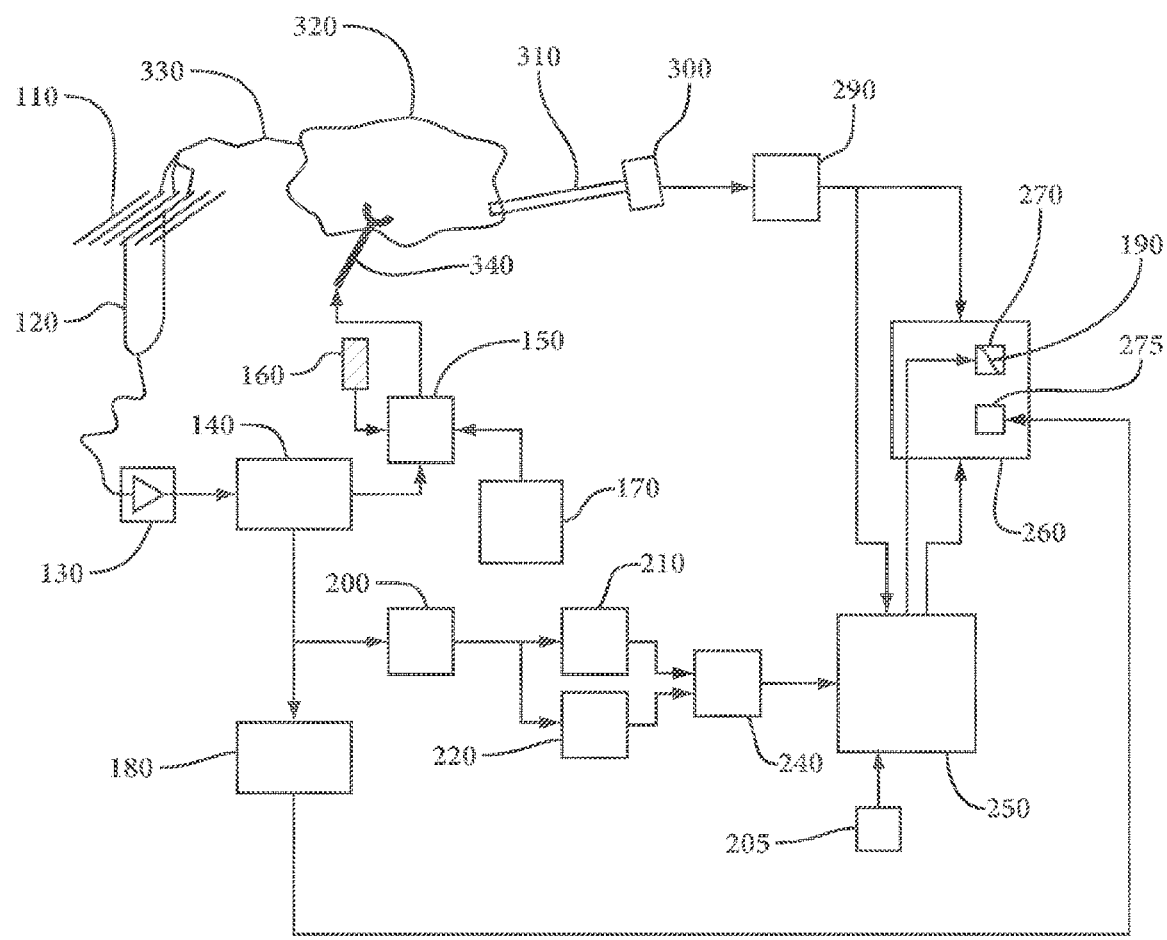
FIG. 2 is an overall schematic illustration of the proposed system and the result integration into a manually operated laparoscopic surgery system.

In the case of a manually operated laparoscopic surgery, FIG. 2 illustrates a somewhat simpler system in which the surgeon can, at any time, return to the position the Optical Element 310 was in when the nerve of interest was mapped by manually moving the optical element until the image and position recognition software in the Image and Position Recognition Processor 250 confirms the real-time image in the Camera 300 matches the image stored in the Image and Position Recognition Processor 250 of the surgical view displayed when the nerve of interest was marked. The surgeon then can re-display the nerve location 190 in surgeon viewfinder 270 by activating a Re-Display Switch 205.

In practice, the method of this application may be described as follows. The method works in close conjunction with a robotic surgery device that has a camera with a positionable optical element presenting an image of the laparoscopic surgical field. It provides at least one electrode probe that is inserted into the body cavity through a surface of the body, the at least one electrode probe being positionable by a laparoscopic device and being operable to couple to the body within the body cavity proximate to a preselected nerve; providing at least one exploratory probe (dual function laparoscopic surgical instrument switched to stimulation mode) separate and distinct from the first at least one electrode probe and adapted to be disposed in the body cavity; introducing an electrical signal via the exploratory probe to the body within the body cavity along a presumed pathway of the nerve of interest thereby depolarizing the tissue surrounding the nerve which results in an action potential that propagates along the nerve to the neuromuscular junction (the synapse between the nerve and the muscle cell) where a neurotransmitter (acetylcholine) is released in response to the action potential. The neurotransmitter depolarizes the postsynaptic muscle cells creating an electrical potential received by the at least one electrode probe, and providing an analyzer interfaced with the at least one electrode probe, the analyzer being operable to indicate the proximity of the at least one exploratory probe to the nerve of interest based on a measurement of the strength of the electrical potential signal sensed by the at least one electrode probe; observing and evaluating the data produced by the analyzer; thus determining the location of the nerve; generating a visual marker of that pathway of the nerve and displaying and storing that visual marker for future reference. The procedure also saves the exact positioning of the optical element during the procedure, allowing a return to the same exact position and a re-displaying of the visual marker image of the nerve pathway.

This combination of improvements enables the surgeon to instantly locate non-visible nerve tissue marked earlier during the surgical procedure so as to know what tissue to spare/not compromise during subsequent surgical intervention and manipulation and to instantly recall previous marked nerve tissue locations.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

What is claimed is:

1. A nerve monitoring system comprising:
   an optical element to connect to a camera;
   at least one recording probe and at least one exploratory probe;
   processors and memories, wherein the processors are coupled to the memories to perform operations comprising:
   in response to communications from the at least one recording probe, indicating proximity of the at least one exploratory probe to a nerve based on a strength of an electrical signal sensed by the at least one recording probe;
   in response to indicating the proximity of the at least one exploratory probe to the nerve, generating and displaying a digital marker representing a location of the nerve within a displayed visual field that is generated while the optical element is at a first physical location;
   in response to the optical element being repositioned from a second physical location back to the first physical location, recognizing an image that was present within the displayed visual field when the optical element was initially at the first physical location;
   in response to recognizing the image that was present on a monitor when the optical element was initially at the first physical location, redisplaying the digital marker within the displayed visual field.

2. The nerve monitoring system of claim 1, wherein the processors are coupled to the memories to perform operations comprising:
   in response to a first user input, generating and displaying the digital marker representing the location of the nerve within the displayed visual field that is generated while the optical element is at the first physical location.

3. The nerve monitoring system of claim 2, wherein the processors are coupled to the memories to perform operations comprising:
   in response to a second user input, redisplaying the digital marker within the displayed visual field.

4. The nerve monitoring system of claim 2, wherein the nerve is not visible within the displayed visual field generated while the optical element is at the first physical location.

5. The nerve monitoring system of claim 1, wherein the processors are coupled to the memories to perform operations comprising:
in response to a user input, returning the optical element to the first physical location.

6. The nerve monitoring system of claim 5, wherein the processors are coupled to the memories to perform operations comprising:
in response to indicating the proximity of the at least one exploratory probe to the nerve, generating and displaying the digital marker representing the location of the nerve within the displayed visual field generated while the optical element is at the first physical location and has a first magnification;
in response to the user input, returning the optical element to the first physical location at the first magnification.

7. The nerve monitoring system of claim 6, wherein the processors are coupled to the memories to perform operations comprising:
in response to indicating the proximity of the at least one exploratory probe to the nerve, generating and displaying the digital marker representing the location of the nerve within the displayed visual field generated while the optical element is at the first physical location and has a first orientation;
in response to the user input, returning the optical element to the first physical location at the first orientation.

8. The nerve monitoring system of claim 6, wherein the processors are coupled to the memories to perform operations comprising:
in response to the user input, redisplaying the digital marker within the displayed visual field.

9. The nerve monitoring system of claim 1, wherein the electrical signal sensed by the at least one recording probe includes an electrical potential or a derivation thereof.

10. A nerve monitoring system comprising:
an optical element to connect to a camera;
at least one recording probe and at least one exploratory probe; and
processors and memories, wherein the processors are to couple to the memories to perform operations comprising:
in response to communications from the at least one recording probe, indicating proximity of the at least one exploratory probe to a nerve based on a strength of an electrical signal sensed by the at least one recording probe;
in response to indicating the proximity of the at least one exploratory probe to the nerve, (a) generating and displaying a digital marker representing a location of the nerve within a displayed visual field that is generated while the optical element is at a first physical location with a first magnification and a first orientation, and (b) storing the first physical location, the first magnification, and the first orientation;
after the optical element is repositioned to a second physical location and in response to a first user input, (a) returning the optical element to the first physical location, the first magnification, and the first orientation, and (b) redisplaying the digital marker within the displayed visual field.

11. The nerve monitoring system of claim 10, wherein the processors are to couple to the memories to perform operations comprising:
in response to a second user input, generating and displaying the digital marker representing the location of the nerve within the displayed visual field that is generated while the optical element is at the first physical location.

12. The nerve monitoring system of claim 10, wherein the nerve is not visible within the displayed visual field generated while the optical element is at the first physical location.

13. The nerve monitoring system of claim 10, wherein the processors are to couple to the memories to perform operations comprising:
introducing an additional electrical signal to tissue via the at least one exploratory probe to create an electrical potential received by the at least one recording probe;
analyzing and displaying the electrical potential;
evaluating the electrical potential to determine the location of the nerve;
wherein the communications from the at least one recording probe include the electrical potential or a derivation thereof.

14. A machine-readable media having stored thereon data, which if used by machines, cause the machines to perform operations comprising:
in response to communications from at least one recording probe, indicating proximity of at least one exploratory probe to a nerve based on a strength of an electrical signal sensed by the at least one recording probe;
in response to indicating the proximity of the at least one exploratory probe to the nerve, generating and displaying a digital marker representing a location of the nerve within a displayed visual field that is generated while an optical element is at a first physical location;
in response to the optical element being repositioned from a second physical location back to the first physical location, recognizing an image that was present within the displayed visual field when the optical element was initially at the first physical location;
in response to recognizing the image that was present on a monitor when the optical element was initially at the first physical location, redisplaying the digital marker within the displayed visual field.

15. The media of claim 14, the operations further comprising:
in response to a first user input, generating and displaying the digital marker representing the location of the nerve within the displayed visual field that is generated while the optical element is at the first physical location.

16. The media of claim 15, the operations further comprising:
in response to a second user input, redisplaying the digital marker within the displayed visual field.

17. The media of claim 14, the operations further comprising:
in response to a user input, returning the optical element to the first physical location.

18. The media of claim 17, the operations further comprising:
in response to indicating the proximity of the at least one exploratory probe to the nerve, generating and displaying the digital marker representing the location of the nerve within the displayed visual field generated while the optical element is at the first physical location and has a first magnification;

in response to the user input, returning the optical element to the first physical location at the first magnification.

19. The media of claim 18, the operations further comprising:

in response to indicating the proximity of the at least one exploratory probe to the nerve, generating and displaying the digital marker representing the location of the nerve within the displayed visual field generated while the optical element is at the first physical location and has a first orientation;

in response to the user input, returning the optical element to the first physical location at the first orientation.

20. The media of claim 19, the operations further comprising:

in response to the user input, redisplaying the digital marker within the displayed visual field.

* * * * *